United States Patent
Bohori et al.

(10) Patent No.: US 8,849,402 B2
(45) Date of Patent: Sep. 30, 2014

(54) SYSTEM AND METHOD FOR CONTACTLESS POWER TRANSFER IN IMPLANTABLE DEVICES

(75) Inventors: Adnan Kutubuddin Bohori, Bangalore (IN); Somakumar Ramachandrapanicker, Bangalore (IN); Suma Memana Narayana Bhat, Bangalore (IN)

(73) Assignee: General Electric Company, Niskayuna, NY (US)

( * ) Notice: Subject to any disclaimer, the term of this patent is extended or adjusted under 35 U.S.C. 154(b) by 330 days.

(21) Appl. No.: 13/052,196

(22) Filed: Mar. 21, 2011

(65) Prior Publication Data

US 2012/0245649 A1   Sep. 27, 2012

(51) Int. Cl.
- A61N 1/00 (2006.01)
- H02J 7/02 (2006.01)
- A61N 1/378 (2006.01)
- H04B 5/00 (2006.01)
- H02J 5/00 (2006.01)

(52) U.S. Cl.
CPC .............. *H02J 7/025* (2013.01); *A61N 1/3787* (2013.01); *H04B 5/0037* (2013.01); *H04B 5/0093* (2013.01); *H02J 5/005* (2013.01)
USPC ................... 607/34; 607/32; 607/33; 607/60; 607/61

(58) Field of Classification Search
CPC ........ A61N 1/3787; H02J 5/005; H02J 7/025; H04B 5/0093; H04B 5/0037
USPC .................................... 607/32, 33, 60, 61, 34
See application file for complete search history.

(56) References Cited

U.S. PATENT DOCUMENTS

| | | | |
|---|---|---|---|
| 5,690,693 | A | 11/1997 | Wang et al. |
| 6,960,968 | B2 | 11/2005 | Odendaal et al. |
| 7,323,964 | B1 | 1/2008 | Shyu et al. |
| 7,471,986 | B2 | 12/2008 | Hatlestad |

(Continued)

FOREIGN PATENT DOCUMENTS

| | | |
|---|---|---|
| EP | 2369711 A2 | 9/2011 |
| JP | 2009106136 A | 5/2009 |
| WO | 2007008646 A2 | 1/2007 |

OTHER PUBLICATIONS

Search Report and Written Opinion from corresponding PCT Application No. PCT/US2012/029326 dated Jun. 27, 2012.

(Continued)

*Primary Examiner* — Michael Kahelin
*Assistant Examiner* — Mallika D Fairchild
(74) *Attorney, Agent, or Firm* — Ann M. Agosti (57) ABSTRACT

A system and method for contactless power transfer in implantable devices for charging rechargeable batteries disposed within the implantable devices are provided. The system includes a first coil electrically couplable to a power source, wherein the first coil is configured to produce a magnetic field. The system further includes a second coil electrically coupled to the rechargeable battery disposed within the implantable device and configured to receive power from the first coil via the magnetic field and to transfer the power to the rechargeable battery. The system also includes a field focusing element disposed between the first coil and the second coil and configured as a self resonant coil having a standing wave current distribution to focus the magnetic field onto the second coil and enhance the coupling between the first coil and the second coil.

17 Claims, 6 Drawing Sheets

(56) References Cited

U.S. PATENT DOCUMENTS

| | | | |
|---|---|---|---|
| 2008/0240358 | A1 | 10/2008 | Utschig et al. |
| 2008/0265684 | A1 | 10/2008 | Farkas |
| 2008/0312852 | A1 | 12/2008 | Mack |
| 2010/0148589 | A1 | 6/2010 | Hamam et al. |
| 2010/0204756 | A1* | 8/2010 | Aghassian .......... 607/60 |
| 2010/0237709 | A1 | 9/2010 | Hall et al. |
| 2010/0308939 | A1 | 12/2010 | Kurs |
| 2011/0140429 | A1 | 6/2011 | Bohori et al. |

OTHER PUBLICATIONS

Zhang et al., "Wireless Energy Transfer Platform for Medical Sensors and Implantable Devices", Engineering in Medicine and Biology Society, Sep. 3-6, 2009, Minneapolis, Minnesota; pp. 1045-1048.

Zhu et al., "Ultrasonic Energy Transmission and Conversion Using a 2-D MEMS Resonator", Electron Device Letters, vol. 31, Issue 4, Apr. 2010, pp. 374-376.

Adnan Bohori et al.; Title : Contactless Power Transfer System; Filed on Apr. 28, 2011; U.S. Appl. No. 12/845,133; 24 Pages.

Adnan Bohori et al.; Title : Contactless Power Transfer System; U.S. Appl. No. 12/845,133, filed Jul. 28, 2010; 34 Pages.

Adnan Bohori et al.; Title : Power Transfer System and Method; U.S. Appl. No. 12/822,232, filed Jun. 24, 2010; 19 Pages.

Stephen Paul Fenton et al.; Title : Electrical Coupling Apparatus and Method; U.S. Appl. No. 12/778,475, filed May 12, 2010; 12 Pages.

Adnan Bohori et al.; Title : System and Method for Contactless Power Transfer in Portable Image Detectors; U.S. Appl. No. 13/149,170, filed Jun. 24, 2010; 19 Pages.

Adnan Bohori et al.; Title : Contactless Power Transfer System; U.S. Appl. No. 12/820,208, filed Jun. 22, 2010; 18 Pages.

Adnan Bohori et al.; Title : Systems for Contactless Power Transfer; U.S. Appl. No. 12/914,512, filed Oct. 28, 2010; 17 Pages.

Adnan Bohori et al.; Title : Contactless Power Transfer System and Method; U.S. Appl. No. 12/731,497, filed Mar. 25, 2010; 27 Pages.

Aristeidis Karalis, J.D. Joannopoulos, Marin Soljac; Title : Efficient wireless non-radiative mid-range energy transfer; Annals of Physics 323 (2008) 34-48.

Shahrzad Jalali Mazlouman, Alireza Mahanfar, Bozena Kaminska; Title: Mid-range Wireless Energy Transfer Using Inductive Resonance for Wireless Sensors; 6 Pages, IEEE International Conference on Computer Design, 2009, ICCD 2009, Oct. 4-7, 2009, Lake Tahoe, CA, pp. 517-522, Digital Object Identifier :10.1109/ICCD.2009.5413106.

\* cited by examiner

FIG. 6

SYSTEM AND METHOD FOR CONTACTLESS POWER TRANSFER IN IMPLANTABLE DEVICES

BACKGROUND

Embodiments of the present invention relate generally to contactless power transfer systems and more particularly to systems for contactless power transfer in implantable devices.

Devices may be implanted in a human body for improving the operation of the human body and increasing life expectancy. The devices that may be implanted in the human body are known as implantable devices. Implantable devices operate on batteries, which may comprise non-rechargeable or rechargeable batteries.

Non-rechargeable batteries typically are replaced after a fixed period of time. Battery replacement surgeries are expensive, complex, and inconvenient to the patient.

However, use of rechargeable batteries are useful for extending the time between battery replacement surgeries. Conventionally, rechargeable batteries are recharged by an inductive coupling system. The inductive coupling system includes a primary coil and a capacitor placed outside the human body and a secondary coil and a capacitor placed inside the body within the implantable device to receive power from the primary coil and recharge the rechargeable battery. Layers of flesh of the human body sometimes result in distances between the primary coil and the secondary coil that reduce the efficiency of the inductive coupling system. Furthermore, the inductive coupling system requires precise alignment of the external charging device with respect to the secondary coil in the implantable device, making the system difficult to use.

Hence, there is a need for an improved system and method to address the aforementioned issues.

BRIEF DESCRIPTION

In one embodiment, a system for contactless power transfer in an implantable device for charging a rechargeable battery disposed within the implantable device is provided. The system includes a first coil electrically couplable to a power source, wherein the first coil is configured to produce a magnetic field. The system further includes a second coil electrically coupled to the rechargeable battery disposed within the implantable device and configured to receive power from the first coil via the magnetic field and to transfer the power to the rechargeable battery. The system also includes a field focusing element disposed between the first coil and the second coil and configured as a self resonant coil having a standing wave current distribution to focus the magnetic field onto the second coil and enhance the coupling between the first coil and the second coil.

In another embodiment, a method for contactless charging of a rechargeable battery disposed in an implantable device is provided. The method includes generating a magnetic field via a first coil coupled to a power source. The method further includes focusing the magnetic field to a second coil via a field-focusing element. The method also includes transferring power from the first coil to the second coil via the magnetic field. The method further includes transmitting the power from the second coil to the rechargeable battery disposed within the implantable device.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Embodiments of the present invention include a system for contactless power transfer in an implantable device for charging a rechargeable battery disposed within the implantable device. The system includes a first coil electrically couplable to a power source. The first coil produces a magnetic field that is coupled to a second coil electrically coupled to the rechargeable battery disposed within the implantable device. The second coil receives the power from the first coil via the magnetic field and further transfers the power to the rechargeable battery. The contactless power transfer system also includes a field-focusing element that is disposed between the first coil and the second coil. The field-focusing element acts as a self-resonant coil having a standing wave current distribution to focus the magnetic field onto the second coil and enhances the coupling between the first coil and the second coil. As used herein, the terms "a" and "an" do not denote a limitation of quantity, but rather denote the presence of at least one of the referenced item.

Figure 1:
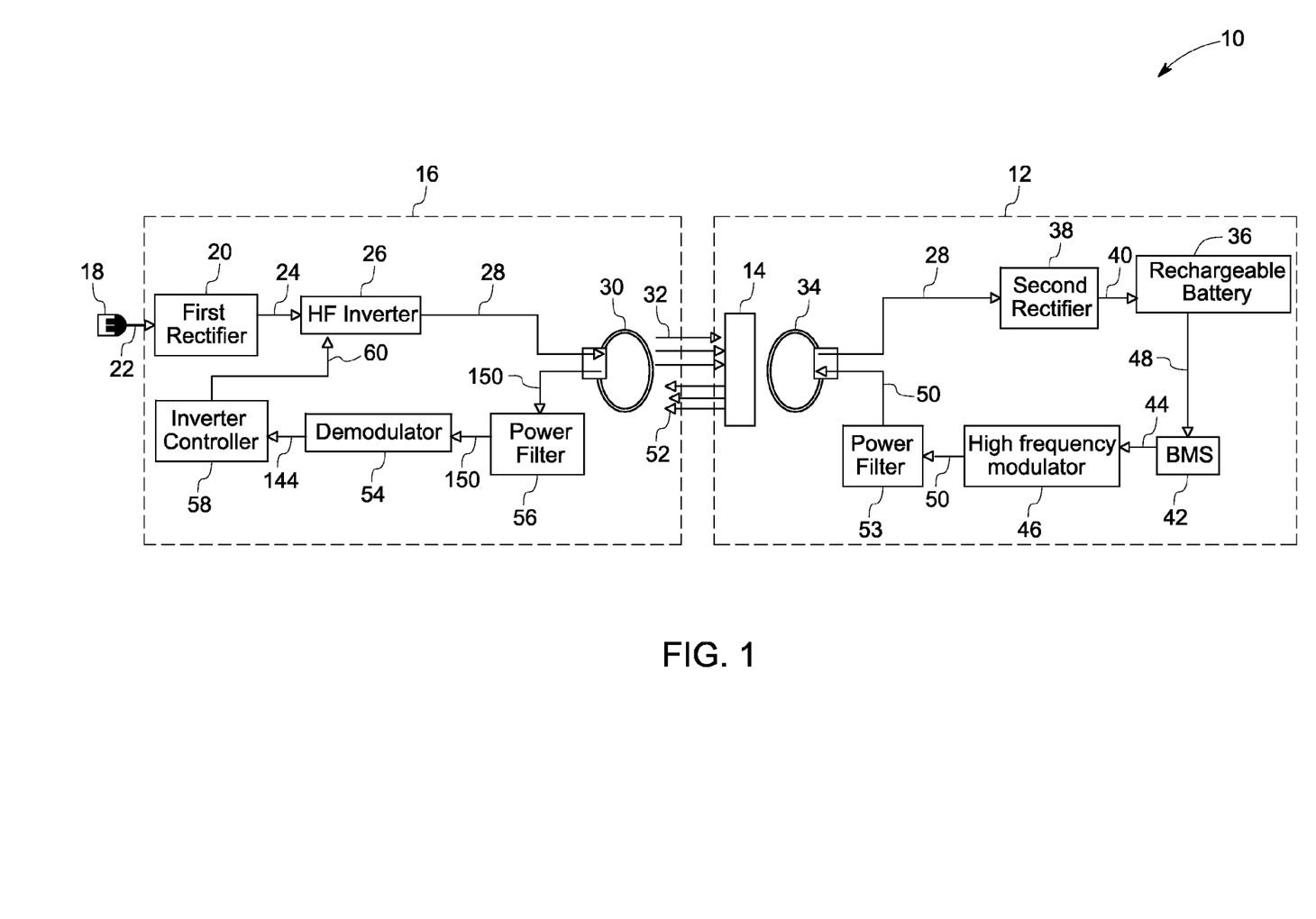
FIG. 1 is a block diagram representation of a system for contactless power transfer in an implantable device including a two channel field-focusing element in accordance with an embodiment of the invention.

FIG. 1 is a block diagram representation of a system 10 for contactless power transfer in an implantable device 12 including a two channel field-focusing element 14 in accordance with an embodiment of the invention. In an exemplary embodiment, the implantable device 12 may include a cardiac pacemaker, a neurological simulator, a muscle simulator, or a cochlear implant. The system 10 further includes a charging device 16.

The charging device 16 includes a power source 18 electrically coupled to a first rectifier 20 that converts AC power 22 received from the power source 18 to DC power 24. The DC power 24 provided by the first rectifier 20 is supplied to a high frequency inverter 26. The high frequency inverter 26 converts the DC power 24 to high frequency AC power 28. In one embodiment, the frequency of AC power 28 includes frequencies that generate minimum heating of human body tissues. In a more specific embodiment, the high frequency AC power has a frequency of at least 1 MHz. The high frequency AC power 28 is further transmitted to a first coil 30 provided in the charging device 16. The first coil 30 receives the high frequency AC power 28 and generates a magnetic field 32 based on the high frequency AC power 28. The charging device 16 may include a stationary charging device or a portable charging device.

The magnetic field 32 is focused on to a second coil 34 provided in the implantable device 12 via a field-focusing element 14 disposed between the first coil 30 and the second coil 34. In the embodiment of FIG. 1, the field-focusing element 14 is situated within the implantable device 16. The field-focusing element 14 acts as a self-resonant coil having a standing wave current distribution to focus the magnetic field 32 on to the second coil 34 and enhances the coupling between the first coil 30 and the second coil 34 as described in commonly assigned U.S. patent application Ser. No. 12/731,497, filed on Mar. 25, 2010 and U.S. patent application Ser. No. 12/914,512, filed on Oct. 28, 2010, which are hereby incorporated by reference in their entirety. In one embodiment, the field-focusing element 14 includes at least one resonator. The at least one resonator may be configured to focus at least one of an electric field, a magnetic field, or an electromagnetic field. In a more specific embodiment, the at least one resonator includes a split ring structure, a circular loop structure, a Koch fractal, an omega structure, or a spiral structure. In an exemplary embodiment, the at least one resonator is disposed within at least one of a dielectric medium, a magnetic medium, or a magneto-dielectric medium. Furthermore, in a particular embodiment, the at least one resonator includes a plurality of resonators with at least two of the plurality of resonators having different resonant frequencies. In one embodiment, the different resonant frequencies enable transfer of power and data signals simultaneously.

The second coil 34 disposed within the implantable device 16, receives the high frequency AC power 28 from the first coil 30 via the magnetic field 32 generated by the first coil 30. In a particular embodiment, the first coil 30 and the second coil 34 are disposed at a distance within a range of about 15 millimeters to about 5 centimeters during the contactless power transfer. The second coil 34 transfers the high frequency AC power 28 to the rechargeable battery 36 electrically coupled to the second coil 34 within the implantable device 16. A second rectifier 38 may be disposed between the second coil 34 and the rechargeable battery 36 to receive the high frequency AC power 28 from the second coil 34 and convert the AC power 28 to DC power 40 before transferring the DC power 40 to the rechargeable battery 36. In one embodiment, the DC power 40 transferred to the rechargeable battery 36 is within a range of about 1 microwatt to about 900 milliwatts.

In the embodiment of FIG. 1, the rechargeable battery 36 is coupled to a battery management system (BMS) 42 that manages the charging of the rechargeable battery 36. In one embodiment, the BMS 42 tracks signals 48 representative of the power levels in the rechargeable battery 36 and calculates the power and time required to charge the rechargeable battery 36. In another embodiment, the BMS 42 regulates a voltage of the DC power 40 entering the rechargeable battery 36. In some embodiments, the BMS 42 communicates with the high frequency inverter 26 disposed within the charging device 16 to provide data 44 related to the voltage and charge level of the rechargeable battery 36.

The BMS 42 is communicatively coupled to a high frequency modulator 46 that receives the data signals 44 generated by the BMS 42 and modulates the data signals 44 to provide modulated data signals 50. The high frequency modulator 46 is coupled to the second coil 34. The second coil 34 converts the modulated data signals 50 to a data magnetic field 52 that is focused on the first coil 30 via the field-focusing element 14. In this embodiment, the field-focusing element 14 includes a two channel field-focusing element including one unidirectional channel to transfer the AC power 28 and a second channel to transfer the data signals 44. A power filter 53 may be disposed between the second coil 34 and the high frequency modulator 46 to isolate the high frequency AC power 28 received from the first coil 30 from the high frequency modulator 46.

The first coil 30 receives the data magnetic field 52 and transfers signals 150 which are representative of the modulated data signals 50 to a demodulator 54. A power filter 56 at the charging device 16 may be used to restrict the high frequency AC power 28 within the first coil 30 from entering the demodulator 54. The demodulator 54 extracts signals 144 representative of the data signals 44 from the modulated data signals 150 and transfers the data signals 144 to an inverter controller 58. The inverter controller 58 controls the voltage and frequency of power at which the high frequency inverter 26 operates in the charging device 16 by providing control signals 60 based on the data signals 144. The inverter controller 58 identifies the voltage and the charge status from the data signals 144 and regulates the inverter operation accordingly to provide desired charging to the rechargeable battery 36.

Figure 2:
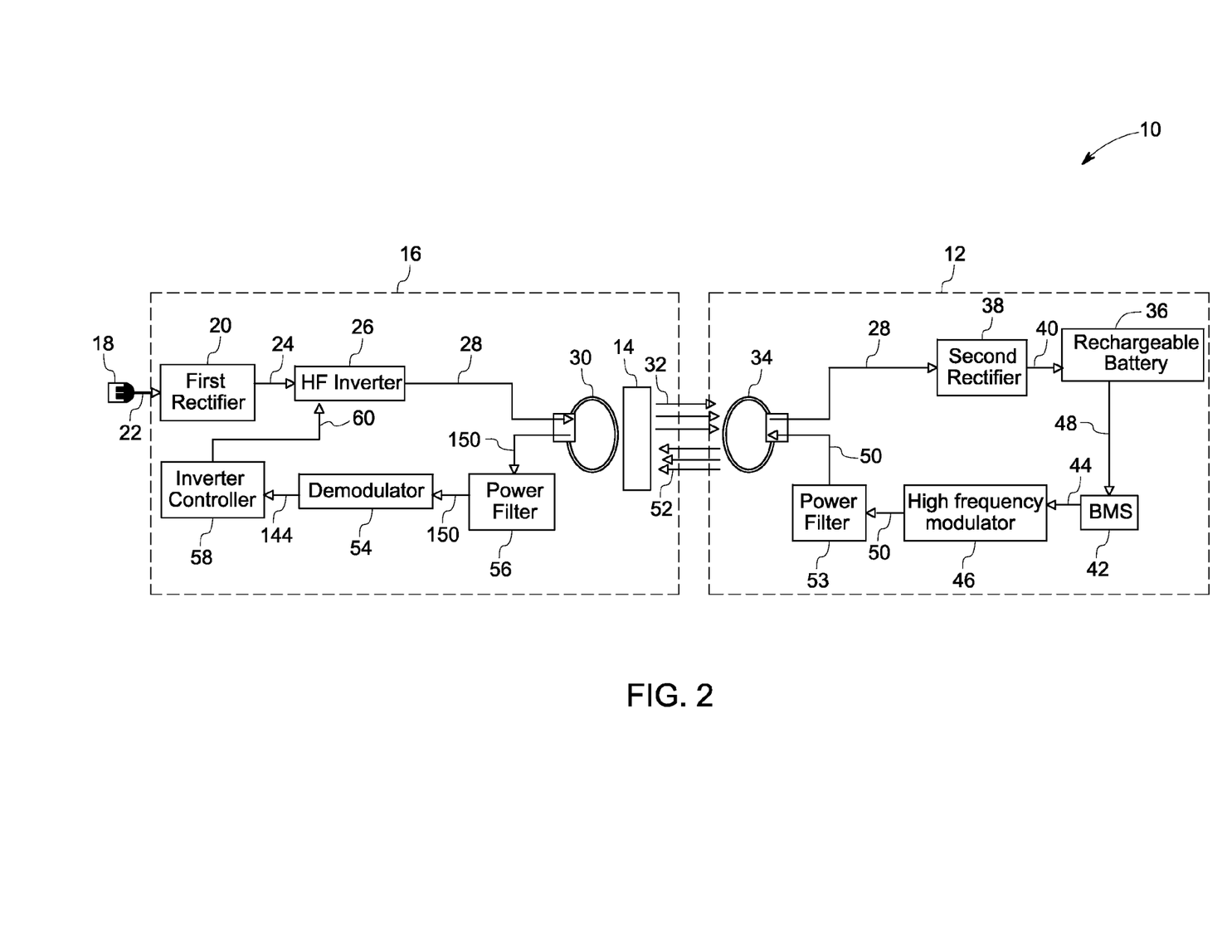
FIG. 2 is a block diagram representation of an alternate configuration of a system for contactless power transfer in an implantable device including a two channel field-focusing element electrically coupled to a first coil in accordance with an embodiment of the invention.

FIG. 2 is a block diagram representation of an alternate configuration of the system 10 for contactless power transfer in an implantable device 12 including the two channel field-focusing element 14 electrically coupled to the first coil 30 in accordance with an embodiment of the invention. In the embodiment of FIG. 2, the field-focusing element 14 is situated within the charging device 16 rather than within the implantable device.

Figure 3:
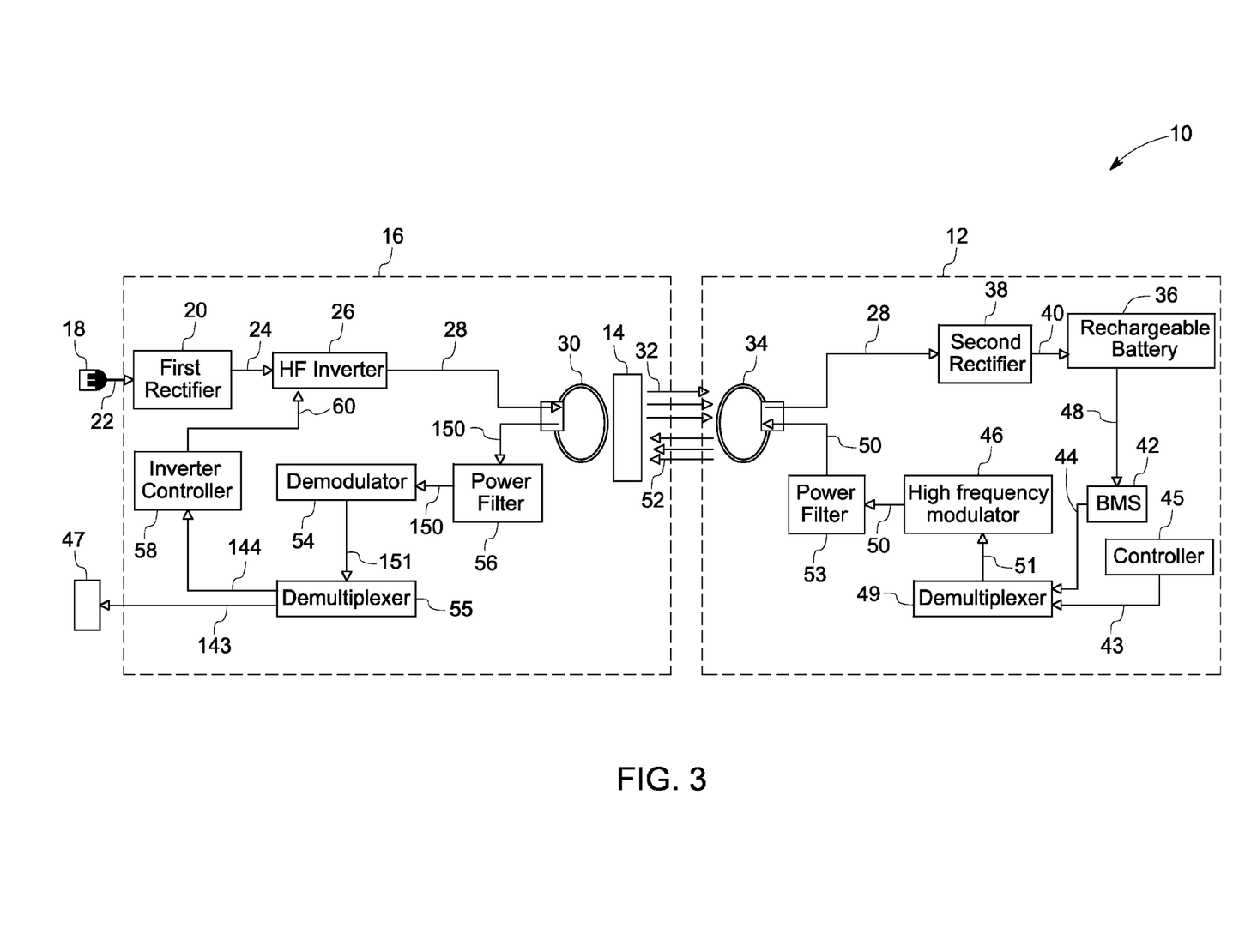
FIG. 3 is a block diagram representation of another alternate configuration of the system for contactless power transfer in an implantable device including a two channel field focusing element configured to transfer data signals and operational data from a controller to an electronic device for medical analysis in accordance with an embodiment of the invention.

FIG. 3 is a block diagram representation of another alternate configuration of the system 10 for contactless power transfer in an implantable device 12 including a two channel field focusing element 14 configured to transfer data signals 44 from battery management system 42 as well as operational data 43 from a controller 45 to an electronic device 47 for medical analysis in accordance with an embodiment of the invention. In this embodiment, the implantable device 12 includes the controller 45, and the controller 45 monitors and controls the operation of the implantable device 12 and stores the operational data 43. The operational data 43 may be used for further analysis such as, for example, prognostic health monitoring of the implantable device 12. In one embodiment, the controller 45 transfers the operational data 43 to a multiplexer 49 that multiplexes the operational data 43 along with the data signals 44 transferred by the BMS 42 to the multiplexer 49. The multiplexer 49 generates a multiplexed signal 51 that is transferred to the high frequency modulator 46 for modulation and is further transmitted to the first coil 30.

The first coil 30 receives the multiplexed signal 151 representative of the multiplexed signal 51 in the implantable device and transfers the multiplexed signal 151 to a de-multiplexer 55 after demodulation by the de-modulator 54 as described above. The de-multiplexer 55 separates the operational data 143 and the data signals 144 from the multiplexed signal 151 representative of the operational data 43 and the data signals 44 in the implantable device 12 respectively. The data signals 144 are transferred to the inverter controller 58 as described above and the operational data 143 may be transferred to the electronic device 47 provided outside the charging device 16 for further analysis.

Figure 4:
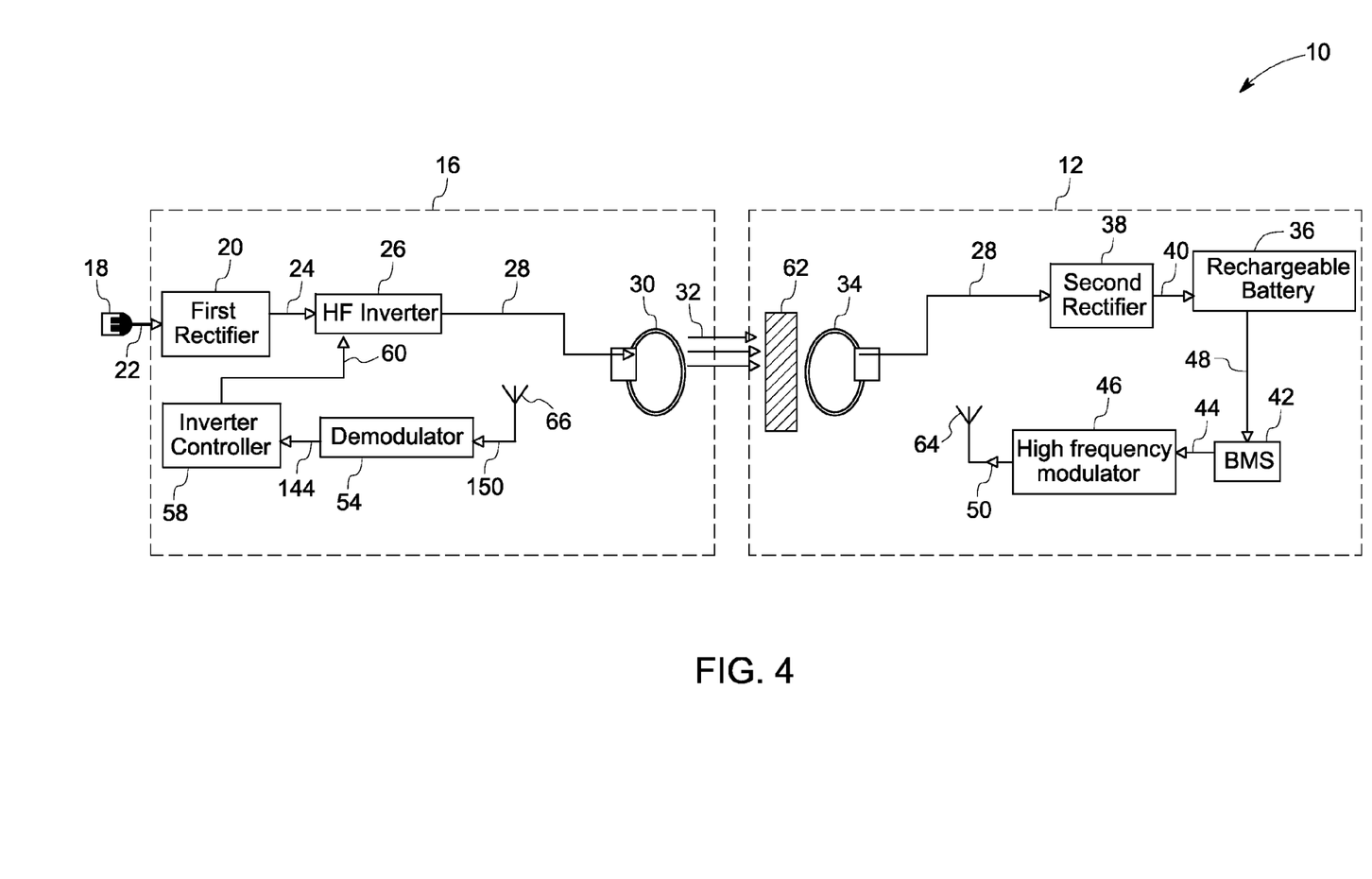
FIG. 4 is a block diagram representation of a system for contactless power transfer in an implantable device including a single channel field-focusing element in accordance with an embodiment of the invention.

FIG. 4 is a block diagram representation of a system 10 for contactless power transfer in the implantable device 12 including a single channel field-focusing element 62 in accordance with an embodiment of the invention. The single channel field-focusing element 62 focuses high frequency AC power 28 from the first coil 30 to the second coil 34 but, in contrast to the embodiments of FIGS. 1 and 2, does not transfer modulated data signals 50 from the second coil 34 to the first coil 30. Although the single channel field-focusing element 62 is shown as being situated in the implantable device, the single channel field-focusing element 62 may alternatively be situated in the charging device. In the embodiment of FIG. 4, the modulated data signals 50 received from the high frequency modulator 46 may be transferred to a RF transmitter antenna 64 disposed within the implantable device 12. The RF transmitter antenna 64 transmits the modulated data signals 50 to a RF receiver antenna 66 disposed within the charging device 16. The RF receiver antenna 66 receives the modulated data signals 150 representative of the modulated data signals 50 from the implantable device 12 and transfers the modulated data signals 150 to the demodulator 54 for further processing as described above.

Figure 5:
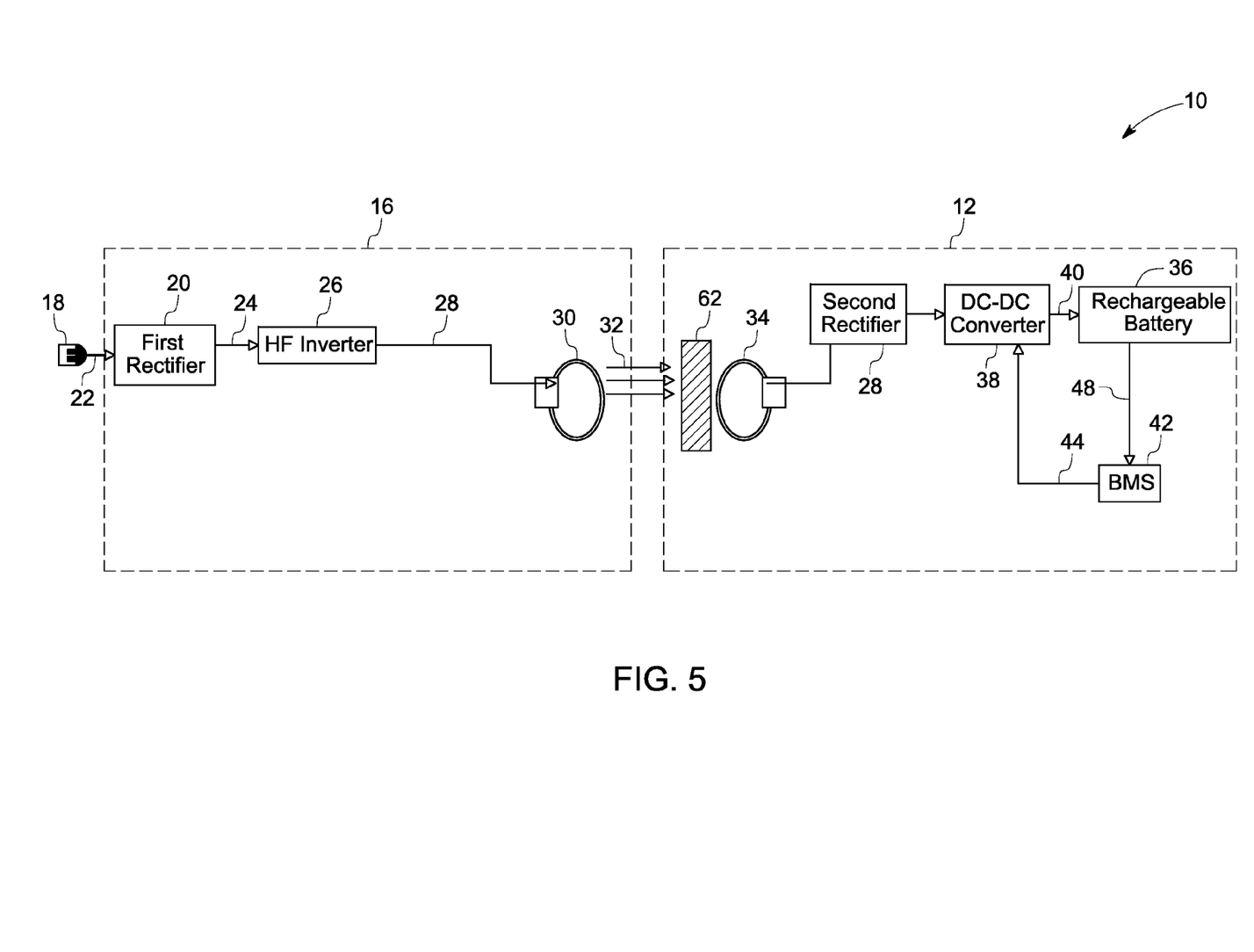
FIG. 5 is a block diagram representation of an alternate configuration of a system for contactless power transfer in an implantable device including a single channel field-focusing element in accordance with another embodiment of the invention.

FIG. 5 is a block diagram representation an alternate configuration of the system 10 for contactless power transfer in the implantable device 12 wherein no data is required to be transmitted back to the charging device 16. The system 10 includes the single channel field-focusing element 62 to focus high frequency AC power 28 from the first coil 30 to the second coil 34. Although the single channel field-focusing element 62 is shown as being situated in the charging device, the single channel field-focusing element 62 may alternatively be situated in the implantable device. The high frequency AC power 28 from second coil 34 is converted to DC power by the second rectifier 38, which is transferred to a DC-DC converter 68, which provides DC power 40. The DC power 40 is fed to the rechargeable battery 36 for charging. The rechargeable battery 36 is coupled to the BMS 42 that regulates the charging of the rechargeable battery 36. In the embodiment of FIG. 5, the BMS 42 is coupled to the DC-DC converter 68 via a feedback loop to regulate the voltage of the DC power 40 entering the rechargeable battery 36 in the implantable device 12. The DC-DC converter 68 receives the data signals 44 from the BMS 42 via the feedback loop and adjusts accordingly to provide optimum charging to the rechargeable battery 36.

Figure 6:
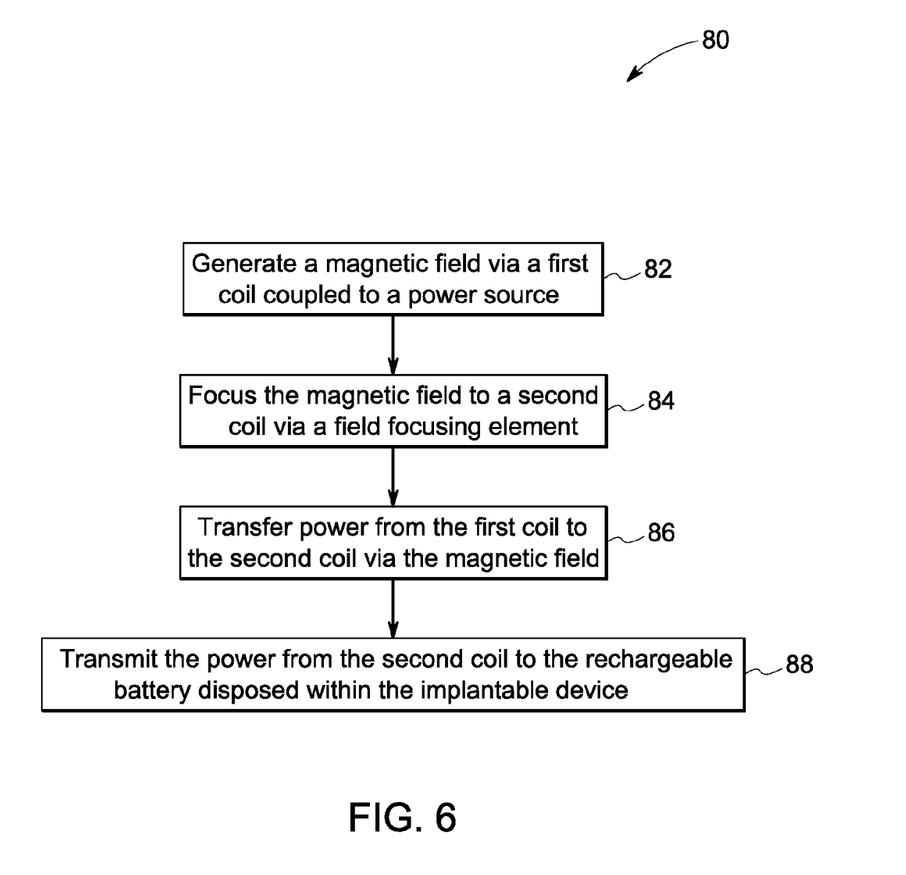
FIG. 6 is a flow chart representing the steps involved in a method for contactless charging of a rechargeable battery disposed in an implantable device in accordance with an embodiment of the invention.

FIG. 6 is a flow chart representing the steps involved in a method 80 for contactless charging of a rechargeable battery disposed in an implantable device in accordance with an embodiment of the invention. The method 80 includes generating a magnetic field via a first coil coupled to a power source in step 82. The magnetic field generated by the first coil is focused to a second coil by employing a field-focusing element in step 84. In one embodiment, the first coil and the second coil are disposed at a distance within a range of about 15 millimeter to about 5 centimeters prior to focusing the magnetic field. The first coil transfers power to the second coil via the magnetic field in step 86. In an exemplary embodiment, the power is transferred from the first coil to the second coil within a range of about 1 microwatt to about 900 milliwatts. The power from the second coil is transmitted to the rechargeable battery disposed within the implantable device in step 88. In one embodiment, data signals regarding the implantable device, the state of charge of the rechargeable battery, or both are obtained and transferred through the field-focusing element, first coil and the second coil to a processor situated outside of the implantable device. In a more specific embodiment, the process is facilitated by having the power and the data signals from the rechargeable battery and implantable device respectively transferred at different resonant frequencies. In still other embodiments, data transfer either is not required or is accomplished via RF transmission.

The various embodiments of the systems for contactless power transfer in implantable devices described above include a power source, a first coil, a field focusing element and a second coil that enable transfer of power via a contactless medium from the first coil to the second coil. The contactless power transfer system enables efficient contactless power transfer between the charging device provided outside the human body and the implantable device disposed inside the human body, for example. The contactless power transfer system also maintains the efficiency in case of multiple layers of flesh provided between the first coil and the second coil. This provides a non-destructive method for charging the rechargeable battery disposed within the implantable device and reduces costs and risks to human life during operations.

It is to be understood that a skilled artisan will recognize the interchangeability of various features from different embodiments and that the various features described, as well as other known equivalents for each feature, may be mixed and matched by one of ordinary skill in this art to construct additional systems and techniques in accordance with principles of this disclosure. It is, therefore, to be understood that the appended claims are intended to cover all such modifications and changes as fall within the true spirit of the invention.

The invention claimed is:

1. A system for contactless power transfer comprising:
   a first coil adapted to be electrically coupled to a power source, wherein the first coil is configured to produce a magnetic field;
   a second coil adapted to be electrically coupled to a rechargeable battery disposed within an implantable device, wherein the second coil is configured to receive power from the first coil via the magnetic field and to transfer the power to the rechargeable battery; and
   a field focusing element disposed between the first coil and the second coil and configured as a self resonant coil having a standing wave current distribution to focus the magnetic field onto the second coil and enhance the coupling between the first coil and the second coil, wherein the field focusing element comprises a plurality of resonators configured to operate at different resonant frequencies and simultaneously focus the magnetic field at different resonant frequencies.

2. The system of claim 1, wherein the contactless power transfer system comprises a charging device and the field focusing element is disposed within the charging device or the implantable device.

3. The system of claim 1, wherein the implantable device comprises a cardiac pacemaker, a neurological simulator, a muscle simulator, or a cochlear implant.

4. The system of claim 1, wherein the second coil is configured to transfer the power within a range of about 1 microwatt to about 900 milliwatts to the rechargeable battery.

5. The system of claim 1, wherein a distance between the first coil and the second coil is within a range of about 15 millimeters to about 5 centimeters.

6. The system of claim 1, further comprising a high frequency inverter coupled between the power source and the first coil.

7. The system of claim 1, wherein the plurality of resonators comprises a split ring structure, a circular loop structure, a Koch fractal, an omega structure or a spiral structure.

8. The system of claim 1, wherein the plurality of resonators is disposed within at least one of a dielectric medium, a magnetic medium, or a magneto-dielectric medium.

9. The system of claim 1, wherein plurality of resonators simultaneously focus the magnetic field at different resonant frequencies to enable simultaneous transfer of power and data signals.

10. The system of claim 1, wherein the field focusing element is configured to focus at least one of an electric field, a magnetic field, or an electromagnetic field.

11. A method for contactless charging of a rechargeable battery disposed in an implantable device comprising:
generating a magnetic field via a first coil coupled to a power source;
simultaneously focusing the magnetic field at different resonant frequencies to a second coil via a field focusing element, wherein the field focusing element comprises a plurality of resonators with at least two of the plurality of resonators configured to operate at different resonant frequencies and simultaneously focus the magnetic field at the different resonant frequencies;
transferring power from the first coil to the second coil via the magnetic field; and
transmitting the power from the second coil to the rechargeable battery disposed within the implantable device.

12. The method of claim 11, wherein transferring the power from the first coil to the second coil comprises transferring the power within a range of about 1 microwatt to about 900 milliwatts.

13. The method of claim 11, further comprising, prior to focusing the magnetic field, disposing the first coil and the second coil at a distance within a range of about 15 millimeters to about 5 centimeters.

14. The method of claim 11, further comprising obtaining data signals regarding the implantable device, the state of charge of the rechargeable battery, or both, and transferring the data signals to a processor situated outside of the implantable device.

15. The method of claim 14, wherein the transferring of the data signals further comprising transferring the power to the rechargeable battery and the data signals from the implantable device at the different resonant frequencies.

16. The method of claim 14 further comprising using the data signals to control the magnetic field generated by the first coil.

17. The method of claim 11, further comprising obtaining data signals regarding the implantable device, the state of charge of the rechargeable battery, or both, and using the data signals to control the power transmitted from the second coil to the rechargeable battery.

* * * * *